US006107285A

United States Patent [19]

Gatti et al.

[11] Patent Number: 6,107,285
[45] Date of Patent: *Aug. 22, 2000

[54] INJECTABLE READY-TO-USE SOLUTIONS CONTAINING AN ANTITUMOR ANTHRACYCLINE GLYCOSIDE

[75] Inventors: Gaetano Gatti, Sesto San Giovanni; Diego Oldani, Robecco sul Naviglio; Giuseppe Bottoni, Bergamo; Carlo Confalonieri, Cusano Milanino; Luciano Gambini, Cornaredo; Roberto De Ponti, Milan, all of Italy

[73] Assignee: Pharmacia & UpJohn Company, Kalamazoo, Mich.

[ * ] Notice: This patent is subject to a terminal disclaimer.

[21] Appl. No.: 07/827,742

[22] Filed: Jan. 29, 1992

Related U.S. Application Data

[62] Division of application No. 07/503,856, Apr. 3, 1990, Pat. No. 5,124,317.

[30] Foreign Application Priority Data

Aug. 2, 1985 [GB] United Kingdom .................... 8519452

[51] Int. Cl.⁷ .................................................. A61K 31/70
[52] U.S. Cl. ............................................. 514/34; 536/6.4
[58] Field of Search ....................... 536/6.4, 34; 424/78; 514/34

[56] References Cited

U.S. PATENT DOCUMENTS

| | | |
|---|---|---|
| 3,590,028 | 6/1971 | Arcamone et al. . |
| 3,686,163 | 8/1972 | Arcamone et al. . |
| 4,035,566 | 7/1977 | Modest et al. . |
| 4,039,633 | 8/1977 | Zelinski . |
| 4,039,663 | 8/1977 | Penco et al. . |
| 4,039,736 | 8/1977 | Bradner et al. . |
| 4,046,878 | 9/1977 | Patelli et al. ............................. 514/34 |
| 4,058,519 | 11/1977 | Arcamore et al. ....................... 514/34 |
| 4,067,969 | 1/1978 | Penco et al. . |
| 4,075,328 | 2/1978 | Ducep et al. . |
| 4,109,076 | 8/1978 | Henry et al. ............................... 536/4 |
| 4,109,079 | 8/1978 | Kawahara et al. . |
| 4,177,264 | 12/1979 | Wu et al. . |
| 4,250,303 | 2/1981 | Wu et al. . |
| 4,296,105 | 10/1981 | Baurain et al. . |
| 4,325,947 | 4/1982 | Penco et al. . |
| 4,327,087 | 4/1982 | Rosenkrantz et al. . |
| 4,438,105 | 3/1984 | Sarato et al. . |
| 4,537,593 | 8/1985 | Alchas ................................... 604/411 |
| 4,564,054 | 1/1986 | Gustavsson ............................ 141/329 |
| 4,576,211 | 3/1986 | Valentini et al. ....................... 141/329 |
| 4,588,403 | 5/1986 | Weiss et al. ............................ 604/411 |
| 4,675,311 | 6/1987 | Gatti et al. . |
| 4,746,516 | 5/1988 | Moro et al. ............................... 514/34 |
| 4,786,281 | 11/1988 | Valentini et al. ....................... 604/256 |
| 4,946,831 | 8/1990 | Gatti et al. ............................... 514/34 |

FOREIGN PATENT DOCUMENTS

| | | |
|---|---|---|
| 1005760 | 2/1977 | Canada . |
| 1041488 | 10/1978 | Canada . |
| 1046507 | 1/1979 | Canada . |
| 1046508 | 1/1979 | Canada . |
| 1204738 | 5/1980 | Canada . |
| 1129344 | 8/1982 | Canada . |
| 1203482 | 4/1986 | Canada . |
| 129606 | 1/1985 | European Pat. Off. . |
| 0 401 896 A1 | 12/1990 | European Pat. Off. . |
| 2 314 725 | 1/1977 | France . |
| 2 432 525 | 2/1980 | France . |
| 29 27 452 | 1/1980 | Germany . |
| 35 36 896 | 4/1986 | Germany . |
| 60-92212 | 10/1983 | Japan . |
| 6092212 | 5/1985 | Japan . |
| 8502869 | 10/1985 | Netherlands . |
| 2 007 645 | 5/1979 | United Kingdom . |
| 2 124 224 | 2/1984 | United Kingdom . |
| 216751 | 4/1986 | United Kingdom . |
| 2 178 311 | 2/1987 | United Kingdom . |
| 985598 | 3/1995 | United Kingdom . |

OTHER PUBLICATIONS

Arcamone et al, "Structure and Physicochemical Properties", Internation Symposium on Adriamycin (1972) pp. 9–22.

Benvenuto et al, *American Journal of Hospital Pharmacy*, vol. 38 Dec. 1981, pp. 1914–1918.

Beijnen et al, *Pharmaceutical Weekblad Scientific Editor*, vol. 7 (1985) pp. 109–116.

Wasserman et al, *International Journal of Pharmaceuticals* vol. 19 (1983) pp. 73–78.

Bosanquet, *Cancer Chemother Pharmacol.* (1986) vol. 17 pp. 1–10.

Electrochemical Properties of Adriamycin Adsorbed on a Mercury Electrode Surface Bull. Chem. Soc. Japan, Sep., 1984; vol. 57, pp. 2383–2390; Kenji Kano, Tomonori Konse, Naomi Nishimura and Tanekazu Kubota.

The Effects of the pH and the Termperature on the Oxidation–reduction Properties of Adriamycin Adsorbed on a Mercury Electrode Surface Bull. Chem. Soc. Japan, Feb. 1985; vol. 58, pp. 424–428; Kenji Kano, Tomonori Konse, and Tanekazu Kubota.

American Journal of Hospital Pharmacy, vol. 38, Dec. 1981, pp. 1914–1918, J. Benvenuto, et al., "Stability and Compatibility of Antitumor Agents in Glass and Plastic Containers".

Rote Liste, 1984, Preparation No. 85 031 (with English translation).

(List continued on next page.)

*Primary Examiner*—Elli Peselev
*Attorney, Agent, or Firm*—McDonnell, Boehnen, Hulbert & Berghoff

[57] ABSTRACT

According to the invention there is provided a sterile, pyrogen-free, ready-to-use solution of an anthracycline glycoside, especially doxorubicin, which consists essentially of a physiologically acceptable salt of an anthracycline glycoside dissolved in a physiologically acceptable solvent therefor, which has not been reconstituted from a lyophilizate and which has a pH of from 2.5 to 6.5. The solution of the invention is particularly advantageous for the administration by injection of the anthracycline glycoside drugs, e.g. doxorubicin, in the treatment of both human and animal tumors.

13 Claims, No Drawings

OTHER PUBLICATIONS

H. Bohme, et al., "Europaisches Arzneibuch III," 1979, p. 654 (with English translation).

*The Interpharm International Dictionary of Biotechnology and Pharmaceutical Manufacturing,* edited by Dean E. Synder, Publisher Buffalo Grove, IL: Interpharm Press, Inc., 1992.

Merck Index, $10^{th}$ edition 1983, p. 499, entry 3,435.

Bosanquet, "Stability of solutions of antineoplastic agents during preparation and storage for in vitro assays", *Cancer Chemotherapy and Pharmacology,* vol. 17, 1986, pp. 1–10.

Rolf Kaltofen, Joachim Ziemann et al., *Tabellenbuch Chemie,* $12^{th}$ edition, pp. 172, 181.

Yüksel, "Determination of Ceftriaxone in Aqueous Humour and Serum Samples by Difrerrential–pulse Adsorptive Stripping Voltammetry", *Analyst,* vol. 119, 1994, pp. 1575–1577.

Falbe et al., *Rompp Chemie Lexikon,* $9^{th}$ edition, Georg Thieme Verlag Stuttgart, New York, 1992, "Buffers", pp. 3677–3678.

Mortimer, *Chemie,* $3^{rd}$ edition, Georg Thieme Verlag Stuttgart, New York, 1980, pp. 490–494.

Tan, C. et al., Daunomycin, an Anti–Tumor Antibiotic, in the Treatment of Neoplastic Disease, Mar. 1967, *Cancer* 20:333–353.

Samuels, L.D. et al., "Daunorubicin Therapy in Advanced Neuroblastoma", Apr. 1971, *Cancer* 27:831–834.

Miller, A.A. and Schmidt, C.G., "Clinical Pharmacology and Toxocology of 4Δ–O–tetrahydropyranyladriamycin", Mar. 1, 1987, *Cancer Research* 47:1461–1465.

Rozencweig, M. et al., "Preliminary Experience with Marcellomycin: Pre–Clinical and Clinical Aspects" p. 5499–561.

Arcamone et al. (1969), "Adriamycin, 14–Hydroxydaunomycin, a New Antitumor Antibiotic from *S. Peucetius* Var. *Caesius,*" *Biotechnology and Bioengineering,* vol. XI, pp. 1101–1110.

Despois et al. (1967), "Isolement D'un Nouvel Antibiotique Doue D'Activite Antitumorale: La Rubidomycine (13.057 R.P.) Identite De La Rubidomycine et de La Daunomycine," *Path. Biol.,* vol. 15, pp. 887–891.

Lokich et al. (1983), "Constant Infusion Schedule for Adrimycin: A Phase I–II Clinical Trial of a 30–Day Schedule by Ambulatory Pump Delivery System," *J. Clinical Oncology,* vol. 1, pp. 24–28.

Wasserman and Bundgaard (1983), "Kinetics of the Acid–Catalyzed Hydrolysis of Doxorubicin," *International J. Pharmaceutics,* vol. 14, pp. 73–78.

Merck Index (1996), Mitoxantrone, 12th Edition, Entry 6303, p. 1064.

Martindale (1989), Mitotone, *The Pharmaceutical Press,* 29th Edition, London, Entry 1852–x, pp. 643–645.

ABPI Data Sheet Compendium, 1994–1995, "Novantron Injection," Lederle Laboratories, pp. 752–754.

Geigy Scientific Tables, vol. 3, *Physical Chemistry Composition of Blood Hematology Somatometric Data,* 8th revised and enlarged edition, Edited by C. Lentner, pp. 54–60.

Chemical Abstracts, vol. 92 (1980), 99512 c.
Chemical Abstracts, vol. 94 (1981), 214489f.
Chemical Abstracts, vol. 99 (1983), 146022z.
Chemical Abstracts, vol. 101 (1984), 122451x.
Chemical Abstracts, vol. 102 (1985), 209266k.
Chemical Abstracts, vol. 104 (1986), 39716d.
Arzneimittel–Forschung, vol. 17 (1967), pp. 934–939.
The Merck Index (1983) p. 3436.

Pharmaceutisch Weekblad, Scientific Edition, vol. 7, Jun. 21, 198 pp. 109–116.

Pharmaceutisch Weekbald, Scientific Edition, vol. 8, Apr. 25, 1986 pp. 109–133.

Journal of Chromatography 299 (1984), pp. 489–494.

Patent Abstracts of Japan (1956), 92212.

Martindale, The Extra Pharmacopoeia (1982), pp. 205–208.

Nor. Pharm. Acta, 45, 61–67 (1983).

J. Pharm. Biomed Anal., 2, 297–303 (1984).

American Journal of Hospital Pharmacy, vol. 38, pp. 483–486, Apr., 1981, G. K. Poochikian, et al., "Stability of Anthracycline Antitumor Agents in Four Infusion Fluids".

International Journal of Pharmaceutics, vol. 23, No. 1, pp. 1–11, Jan., 1985, M. J. H. Janssen, et al., "Doxorubicin Decomposition on Storage. Effect of pH, Type of Buffer and Liposome Encapsulation".

The United States Pharmacopeia, Twentieth revision, p. 266, Jul. 1, 1980.

Chemical Abstracts, vol. 88, p. 396, No. 197, p. 396, No. 197526X, 1978, T. Kaniewska, "Study of the Decomposition of Adriamycin".

Journal of Pharmaceutical Sciences, vol. 67, No. 6, pp. 782–785, Jun., 1978, S. Eksborg, "Extraction of Daunorubicin and Doxorubicin and Their Hydroxyl Metabolites: Self–Association in Aqueous Solution".

Journal of Pharmaceutical Sciences, vol. 73, No. 6, pp. 766–770, M. Memozzi, et al., "Self–Association of Doxorubicin and Related Compounds in Aqueous Solution".

International Symposium on Adriamycin, pp. 9–22, 1972, F. Arcamone, et al., "Structure and Physicochemical Properties of Adriamycin (Doxorubicin)".

Journal of Pharmaceutical and Biomedical Analysis, vol. 2, No. 2, pp. 297–303, 1984, S. Eksborg, et al., "Liquid Chromatography in Anticancer Drug Research with Special Reference to Anthraquinone Glycosides".

American Journal of Intravenous Therapy and Clinical Nutrition, vol. 8, No. 4, pp. 15–18, 1981, D. Ketchman, et al., "Cost Benefit and Stability Study of Doxorubicin Following Reconstitution".

Analytical Profiles of Drug Substances, vol. 9, pp. 245–274, 1980, A. Vigevani, et al., "Doxorubicin".

The Korean Pharmacopeia, 4 pages, 1977, Section "Injections".

The Guidelines for Examination for Each Industrial Field, Chapter "Medicament", 4 pages.

International Journal of Pharmaceutics, vol. 14, pp. 73–78, 1983, K. Wasserman, et al., Kinetics of the Acid–Catalyzed Hydrolysis of Doxorubicin.

American Journal of Hospital Pharmacy, vol. 36, pp. 1536–1538, 1979, D. M. Hoffman, et al., "Stability of Refrigerated and Frozen Solutions of Doxorubicin Hydrochloride".

Pharmaceutical Society of Japan Journal, vol. 104, No. 6, pp. 614–623, Jun., 1984, T. Masuike, et al., "Determination of Adriamycin and its Metabolities in Biological Samples Using High Performance Liquid Chromatography. I. Analysis of Serum and Plasma by Direct Injection Method. II. Analysis of Tissues by Extraction Method".

American Journal of Hospital Pharmacy, vol. 38, pp. 483–486, Apr., 1981, G. K. Poochikian, E et al., "Stability of Anthracycline Antitumor Agents in Four Infusion Fluids".

Dorr (1979), "Incompatibilities with Parenteral Anticancer Drugs," *The American Journal of Intravenous Therapy,* Feb./Mar., pp. 42, 45–46, 52.

Bernard, J., et al. (1969) *Rubidomycin,* Springer–Verlag, Berlin–Heidelberg–New York.

Karlsen, J., et al. (1983), "Stability of Cytotoxic Intravenous Solutions Subjected to Freeze–Thaw Treatment", *Nor. Pharm Acta,* vol. 45, pp. 61–67.

Vogelzang, N.J., et al. (1985), "Phase I Trial of an Implanted Battery–Powered, Programmable Drug Delivery System for Continuous Doxorubicin Administration," *Journal of Clinical Oncology,* vol. 3, No. 3 (Mar.), pp. 407–414.

Falk, K., et al. (1979), "Mutagenicity in Urine of Nurses Handling Cytostatic Drugs", *The Lancet,* Jun. 9, 1979, pp. 1250–1251.

"Union Warns of Cancer Drug Dangers", *Chemistry and Industry,* Jul. 4, 1983.

Lassila, O., et al. (1980), "Immune Function in Nurses Handling cytostatic Drugs", *The Lancet,* Aug. 30, 1980., p. 482.

Abstract of Medical Economics Co., *Chemistry–Industry,* Feb. 7, 1983, p. 99.

*Chemical Abstract,* vol. 99, p. 345 (1983), Abst. No. 99:218014y.

*Topics in Antibiotic Chemistry,* 2, 109–115, 1978.

Young et al.. The Anthracycline Antineoplastic Drugs (1981) vol. 305(3) New England J. Med 139.

Casazza, Experimental Studies on New Anthracyclines (1984) (Proc. of Int. Symposium on Adriamycin: Ogawa et al. eds.).

Aubel Sadron et al., Daunorubicin and doxorubicin, anthracycline antibiotics, a physicochemical and biological review (1984) Biochemie 66, pp. 333–352.

Abdella et al., A Chemical perspective on the Anthracycline Antitumor Antibiotics, Env. Health Persp. vol. 64, pp. 3–18 (1985).

Arcamone, Daunomycin and Related Antibiotics. Topics in Antibiotic Chemistry. vol. 2 (Sammes, ed.) (1978).

Brown, Adriamycin and Related Anthracycline Antibiotics, Prog. Med. Chem. 15:124 (1978).

Goormagtigh et al., Anthracycline Glycoside–Membrane Interactions, Biochem. Biophys. Acta: 271–288 (1984).

Skovsgaard et al., Adrimycin, An Antitumor Antibiotic : A Review with Special Reference to Daunomycin, Dan. Med. Bull 22(2):62 (1975).

Bachur et al., Cellular pharmacodynamics of several anthracycline antibiotics (1976) J. Med. Chem 19(5):651.

Suarato, "Antitumor Anthracyclines", *The Chemistry of Antiumour Agents* (1990) (Wilman, ed.).

Legha; "The Anthracyclines and Mitoxantrone", *Cancer Chemotheraphy by Infusion* $2^{nd}$ edition (Lokich et.) (1990) Precept Press.

Bouma et al., Anthracycline Antitumor agents: A review of physcicochemical, analytical and stability properties Pharm. Weekblad Sc. Ed., vol. 8, p. 109 (1986).

Williams, Stabillity & Compatibility of Admixtures of Antineoplastic Drugs, *Cancer Chemotherapyhy by Infusion.* $2^{nd}$ Edition (Lukich et.) (1990) Precept Press.

Williams et al., Photoinactivation of Anthracyclines (1981) Photochemistry & Photobiology, vol. 34, p. 131.

Poochikian et al., Stability of anthracycline antitumor agents in four infusion fluids (1981) Chemical Abstracts, vol. 94.214489f.

Keusters, et al., Stability of solutions of doxorubicin and epirubicin in plastic mini bags for intravesical use after storage at −20° C. and thawing by microwave radiation. (1986) Pharm. Weekblad Sc.Ed. vol. 8 p. 144.

Bekers et al., Effect of cyclodextrins on anthracycline stability in acidic aqueous media (1988) Pharm. Weekblad. S. Ed., vol. 10.,207.

Wood, Mary Jayne: Stability of anthracycline cytotoxic agents in solution and infusion fluids–submitted for the degree of Master of Philosophy (The University of Aston in Birmingham). Oct. 1988.

Wood et al., Stability of Doxorubicin, Daunorubicin and Epirubxcin in Plastic Syringes and Minibags (1990) J. Clin. Pharm. Therapeutics vol. 15. p. 279–289.

Crom et al., Pharmacokinetics of Anticancer Drugs in Children, Clin. Pharm. 12:pp. 168–213 (1987).

Greidanus, et al., "Continuous Infusion of Low–dose Doxorubicin, Epirubicin and Mitoxantrone", *Cancer Chemotherapy: A Review,* (1988) Pharm. Weekblad. Sci. Ed., vol. 10, p. 237.

Bachur et al., Daunorubicin and adriamycin metabolism in the golden syrian hamster (1973) Biochem. Med. vol. 8, p. 352.

Haneke et al., Quanititation of Daunorubicin, Doxorubicin, and their Aglycones by Ion–Pair Reversed–Phase Chromarography, J. Pharm. Sci. 70(10): 1112 (1981).

Tomlinson et al., Concomitant Adsorption and Stability of Sonic Anthracycline Antibiotics (Oct. 1982) 71 (10) J. Pharm Sci. 1121.

Von Hoff et al., Daunomycin: An Anthracycline Antibiotic Effective in Acute Leukemia, Adv. Pharm. Chemo. 15:1 (1978).

Cassinelli et al., La Daunomicina: Un Nuovo Antibiotico Ad Attivita Citostatica Isolamento E Proprieta (1963) Giorn. Microbial. 11:167.

Arcamone, La Constitution Chimique de la Daunomycine, Path. Biol. 15(19–20): 893 (1967).

Di Marco et al., Daunomycin, a New Antibiotic of the Rhodomycin Group, Nature 201: 706 (1964).

Angiuli et al., Structure of Daunomycin, X–Ray Analysis of N–Br–Acetyl–Daunomycin Solvate, Nature New Biol., 234:78 (Nov. 1971).

Trissel et al.; Investigational Drug Information (1978) Drug Intell. Clin. Pharm vol. 12, p. 404.

Handbook on Injectable Drugs (Trissel) $2^{nd}$ Ed. 1980, p. 562.

Handbook on Injectable Drugs (Trissel) $5^{th}$ Edition (1988), p. 222–223.

AHFS Drug Information 1984, p. 249–250.

AHFS Drug Information 1990, p. 501–503.

Fischer et al., The Cancer Chemotherapy Handbook $3^{rd}$ Edition (1989), p. 65–69.

Drug Information for the Health Care Professional USP DI 1991—$11^{th}$ Edition, p. 1080–1084.

Beijnen, et al., Structure Elucidation and Characterization of Daunorubicin Degradation Products (1987) Int. J. Pharm., vol. 34, p. 247.

Bachur, Daunomycin Metabolism in Rat Tissue Slices., J. Pharm. Exp. Ther. 175(2):331.

Riley, et al., Review of New Drugs—1980, U.S. Pharm. 33 (Feb.1981).

Boiron et al., Daunorubicin in the Treatment of Acute Myelocytic Leukemia. The Lancet. (Feb. 1969), p. 330.

Di Marco et al., Activity of Adriamycin (NSC 123127) and Daunomycin (NSC 82151) Against Mouse Mammary Carcinoma, Cancer Chemother. Rep., part 1, vol. 56(2):153 (1972).

Barthelemy–Clavey et al., Self–Association of Daunorubicin, FEBS Lett., vol. 46(1), p. 5 (1974).

Calendi et al., On Physico–Chemical Interactions between Daunomycin and Nucleic Acids, Biochem Biophys. Acta., vol. 103:25. (1965).

Schreier, Binding of Daunomycin to Acidic Phospholipids J. Par. Sci. Tech, vol. 43, No. 4, p. 213 (1989).

Dubost et al., Un nouvel antibiotique a proprieties cytostatiques: la rubidomycine (1963) C.R. Acad. Sci. Paris, 257, p. 813.

Maral et al., Etude Toxicologique et activite Antitumorale Experimentale de la Rubidomycine (13.057 R.P.) Path. Biol., vol. 15, No. 19–20, pp. 903–908 (1967).

Depois et al: Un nouvel antibiotique dove d'activite antitumorale la rubidomycine (13.057 R.P.), J. Preparation et properties, Arzicial Forsch. 17:934 (1967).

Brazhnikova et al., Physicochemical Properties of Antitumour Antibiotic Rubomycin produced by Act. Cocruleorubidus (1986) Antibiotki 11:763.

"Discovery & Development of Doxorubicin", *Doxorubicin, Anticancer Antibiotics* (Arcamone, eds.) (1981) Academic Press, pp. 1–47.

Blum et al., Adriamycin: A New Anticancer Drug with Significant Clinical Activity, Annals of Int. Med., 80:249–259 (1974).

Arcamone et al., Adriamycin (14–Hydroxydaunomycin), a Novel Antitumor Antibiotic Tetrahedron Letters No. 13, p. 1007–1010.

Di Marco et al., Adriamycin, a New Antibiotic, Antitumour, Activity, Cancer Chem. Reports, part 1, vol. 53, No. 1, p. 33 (1969).

Trissel: A Handbook on Injectable Drugs $2^{nd}$ edition (1980), p. 196.

Trissel: A Handbook on Injectable Drugs $4^{th}$ edition (1986), p. 215–217.

Trissel: A Handbook on Injectable Drugs $5^{th}$ edition (1988), p. 259–264.

McEvoy, AHFS Drug Information 1984, p. 251–254.

AHFS Drug Information 1990, p. 504–507.

Fischer, The Cancer Chemotherapy Handbook $3^{rd}$ edition (1989), p. 82–87.

Drug Information for the Health Care Professional USP DI (1991) $11^{th}$ Edition, p. 1217–1222.

Benvenuto et al., Stability & Compatibility of Antitumor Agents in Glass & Plastic Containers, (Dec. 1981), Am. J. Hosp. Pharm., vol. 38, p. 1914.

Walker et al., Doxorubicin Stability in Syringes and Glass Vials and Evaluation of Chemical Contamination, Can J. Hosp. Pharm. 44(2): 71(1991).

Gupta et al., Investigation of the Stability of Doxorubicin Hydrochloride using Factorial Design, Drug Development & Industrial Pharmacy, (1988) vol. 14(12) p. 1657–1671.

Beijnen et al., Stability of intravenous admixtures of doxorubicin and vincristine. Am. J. Hosp. Pharm., vol. 43, p. 3022, (Dec. 1986).

Asker et al., Effect of Glutathione on Photolytic Degradation of Doxorubicin Hydrochloride, J. Par. Sci. Tech. (1988), 42(5)193.

Habib et al., Photostabilization of doxorubicin Hydrochloride with Radioprotective and Photoprotective Agents: Potential Mechanism for Enhancing Chemotherapy during Radiotherapy (Nov.–Dec. 1989) 43 J. Parenteral Science & Technology, vol. 43, No. 6, p. 254, (Nov.–Dec,. 1989).

Speth, et al., Clinical Pharmacokinetics of Doxorubicin, Clin. Pharm., vol. 15, pp. 15–31, (1988).

Yee et al., Adriamycin: A Brief Review (Apr., 1981) Am. J. Int. Ther. Clin Nut. pp. 7–12.

Hoffman et al., Stability of Refrigerated and Frozen Solutions of Doxorubicin Hydrochloride (Nov. 1979), Am. J. Hosp. Pharm. vol. 36(11) 1536–1538.

Karlsen et al., Stability of cytotoxic intravenous solutions subjected to freeze–thaw treatment (1983), Chemical Abstracts, vol. 99, No. 146022, p. 374.

Gaj., et al., Compatibility of Doxorubicin Hydrochloride and Vinblastine Sulfate—The Stability of a Solution Stored in Cormed ®Reservoir Bags or Monoject® Plastic Syringes (May, 1984) Am. J. IV Ther. Clin. Nut., p. 8.

Tavoloni et al., Photolytic Degradation of Adriamycin (1980) Comm. J. Pharm. Pharmacol. vol., 32, p. 860.

Garnick et al., Phase 1 Trial of Long Term Continuous Adriamycin Administration, Proc. Am. Soc. Clin. Oncol., C–106: p. 359, (Mar. 1981).

Lokich et al., Constant Infusion Schedule for Adriamycin: A Phase I–II Clinical Trial of a 30–Day Schedule by Ambulatory Pump Delivery System, J. Clin. Oncol., vol. 1 (1): 24 (1983).

Vogelzang et al., Continuous Doxorubicin Infusion (CDI) Using an Implanted Lithium Battery–Powered Drug Administration Device System, Proc. Am.Soc. Clin.Uncol. C–1030: p. 263, (Mar. 1984).

Legha et al., Reduction of Doxorubicin Cardiotoxicity by Prolonged Continuous Intravenous Infusion, Ann. Int. Med., vol. 96, No. 2, p. 133 (1982).

Pavlik et al., Stability of Doxorubicin in Relation to Chemosensitivity Determinations: Loss of Lethality and Retention of Antiproliferative Activity (1984), Cancer Investigation 2 (6), 449–458.

Dozier et al., Practical Considerations in the Preparation and Administration of Cancer Chemotherapy (Sep. 1983) Am.J. Int. Ther. Clin. Nut., p. 6.

Kirschenbaum et al: Stability of injectable medications after reconstitution, Am. J. Hosp. Pharm.: 33:767–790 (Aug., 1976).

Janssen et al., Doxorubicin decomposition on storage. Effect of pH., type of buffer and liposome encapsulation, (1985) Chemical Abstracts, vol. 102, No. 209226k.

Crommelin et al., Preparation and characterization of doxorubicin–containing liposomes. II. Loading capacity, long–term stability and of doxorubicin–bilayer interaction mechanism (1983) Int. J. Pharm. vol. 17, p. 135.

Van Bommel, et al., Stability of Doxorubicin–Liposomes on Storage: as an Aqueous Dispersion, Frozen or Freeze dried (1984), Int. J. Pharm., vol. 22, pp. 299–310.

Crommelin et al., Preparation and characterization of doxorubicin–containing lipsomes: I. Influence of liposome charge and pH of hydration medium on loading capacity and particle size, (1983), Int. J. Pharm., vol. 16, pp. 93–96.

Gupta et al., "Influence of Stabilization Temperature on the Entrapment of Adriamycin", *Albumin Microspheres Drug. Dev. Int. Pharm.*, vol. 13, No. 8, pp. 1471–1482, (1987).

Yanagawa et al., Stability and Releasibility of Adriamycin Ointment (1983).

Vilallonga et al: Interaction of Doxorubicin with Phospholipid Monolayers, J. Pharm. Sci. 67(6), p. 773 (1978).

Duarte–Karim et al., Affinity of adriamycin to phospholipids. A possible explanation for cardiac mirochonorial lesions., (1976) Biochem Biophy. Research Comm., 71(2), p. 658.

Bonadonna et al., Clinical Evaluation of Adriamycin a New Antitumor Antibiotic, Br. Med. J., (3), 503 (Aug. 1969).

Banks et al., Topical Installation of Doxorubicin Hydrochloride in the Treatment of Recurring Superficial Transitional Cell Carinoma of the Bladder, J. Ulrol., vol. 118, p. 757 (1977).

Bertazzoli et al., Chronic toxicity of adriamycin: a new antineoplastic antibiotic (1972), Tox. Applied Pharm., vol. 2, pp. 287–301.

Wang et al., Therapeutic effect and toxicity of adriamycin in patients with neoplastic disease, (1971) Cancer, 28, p. 837.

Horn et al., Intravesical chemotherapy in a controlled trial with thio–tepa versus doxorubicin hydrochloride (1981) J. Urol., 125:652.

Jacobi et al., Studies on the intravesical action of topically administered G3H–doxorubicin hydrochloride in men: plasma uptake and tumor penetration (1980), J. Urol. 124:34.

Jaenke, R.S.: Delayed and progressive myocardial lesions after adriamycin administration in the rabbit. (1976) Cancer Res. vol. 36, pp. 2958–2966.

Casazza et al., Tumors and dental ocular abnormalities after treatment of infant rats with adriamycin, (1977) Tumor 63:331.

Barranco et al., Survival and cell kinetics effects of adriamycin on mammalian cells, (1973). Cancer Res. 33:11.

Gaj et al., Evaluation of growth in Five Microorganisms in Doxorubicin and Floxuridine Media, (1984) Pharm. Manuf., p. 50.

Sturgeon and Schulman: Electronic Absorption Spectra and Protolytic Equlibria of Doxorubicin: Direct Spectrophotometric Determination of Microconstants, J. Pharm. Sci. 66(7):958, (1977).

Dalmark et al., A Fickian Diffusion Transport Process with Features of Transport Catalysis, J. Gen Physiol. 78:349 (1981).

Masuike et al., Determination of Adriamycin and its Metabolities in Biological samples using high performance liquid chromatography Chemical Abstracts (1984), vol. 101, p. 5.

Barth et al., "Determination of Doxorubicin Hydrochloride.", Pharamaceutical Preparations using High Pressure Liquid Chromatography, (1977) J. of Chromatography vol. 131, p. 375–381.

Arena et al., Analysis of the pharmacokinetic characteristics, pharmacological and chemotherapeutic activity of 14–hydroxy–daunomycin (adriamycin), a new drug endowed with an Antitumor activity, (1971) Drug Res. 21: 1258.

Watson et al., Rapid analytic method for adriamycin and metabolites in human plasma by a thin fim flourescence scanner (1976) Cancer Treat. Rep., vol. 60, No. 11, p. 1611.

Langone et al., Adriamycin and Metabolites: Separation by High Pressure Liquid Chromatography and Qunitation by Radioimmunossay, Biochem Med. 12:283 (1975).

Benjamin et al., Pharmacokinetics and metabolism of adriamycin in man, Clin. Pharm. Ther., 14(4) Part 1, 592.

Epirubicin, Drugs of the Future, vol. 8,(5): p. 402, (1985).

Cersosimo et al., Epirubicin: A Review of the Pharmacology, Clinical Activity , and Adverse Effects of an Adriamycin Analogue, J. Clin. Oncol 4(3), 425 (1986).

Fischer, "The Cancer Chemotherapy Handbook", $3^{rd}$ Edition, (1989), p. 87–89.

DeVroe, et. al., A Study on the stability of three antineoplastic drugs and on their sorption by i.v. delivery systems and end–line filters, (1990), Int. J. Pharm. vol. 65, p. 49–56.

DeVries, et. al., A Phase 1 and Pharmocokinetic Study with 21 day Continuous infusion of Epirubicin., J. Clin. Oncol., (1987), 5(9), 1445–1451.

Adams, et. al, Pharmaceutical Apsects of Home Infusion Therapy for Cancer Patients, (Apr. 1987), Pharm J., p. 476.

Weenen, et. al., "Pharmacokinetics of 4–Epi–doxorubicin in Man", Invesi. New Drugs, vol. 1, (1983), p. 59.

Arcamone, et. al., "Synthesis and Antitumour Activity of 4–Demethoxydaunorubicin, 4–Demothoxy-7,9–diepidaunorubicin, and their beta anomers", Cancer Treat Rep. 60(7):829 (1976).

Turowski et al., "Visual Compatability of Idarubicin Hydrochloride with selected drugs during simulated Y–site injection", (Oct. 1991), Ans. J. Hosp. Pharm., vol. 48, p. 2181.

Hurteloup et al., Phase II Trial of Idarubicin (4–Demethoxydaunorubicin) in Advanced Breast Cancer, Eur. J. Cancer Clin. Oncol. 25(3)423 (1989).

Kaplan et al., Phase I Trial of 4– Demethoxydaunorubicin with single i.v. doses, Eur. J. Clin. Cancer Oncol., 18(12) 1303 (1982).

Reich et al., "Carminomycin, Arptheacyclines: Current Status and New Developments,"(1980) (J. Cooke et al., eds.) Academic Press, p. 295.

Brazhnikova et al., "Physical and Chemical Characteristics and Structure of Carminomycin, a New Antitumour Antibiotic", J. Antibiot, 27(4):254 (1974).

Brazhnikova et al., "Carminomycin, a New Antitumour Anthracycline" (1973) Antibiotiki 18:681.

Crooke, "A Review of Carminomycin, A New Anthracycline Developed in the USSR" J. Med. 8(5):295 (1977).

Lankelma et al, "Plasma Concentrations of Carminomycin and Carminomycinol in Man, Measured in High Pressure Liquid Chromatography", Eur. J. Cancer clin. Oncol. 18(4):363 (1982).

Fandrich, "Analysis of Carminomycin in Human Serum by Fluorometric High–Performance Liquid Chromatography", J. Chromatogr. 223 115 (1981).

Oki, "Aclacinomycin A Anthracyclines: Current Status and New Developments", (1980) Academic Press., p. 323.

Oki et al., "Antitumour Anthracycline Antibiotics, Aclacinomycin A and Analogues: I. Taxonomy, Production, Isolation and Physicochemical Properties", J. Antibiot 32(8):791 (1979).

Oki, "New Antitumour Antibiotics, Aclacinomycins A and B", J. Antibiot, 28(10):830 (1975).

Mori et al., "Physicochemical Properties and Stability of Aclacinomycin A Hydrochloride," (1980), Jpn. J. Antibiot 33:618.

Trissel, "Handbook on Injectable Drugs", $5^{th}$ Edition, p. 707.

Fischer, "The Cancer Chemotherapy Handbook", $3^{rd}$ Edition, pp. 17–19.

Arcamone et al., "Synthesis and Antitumour Activity of 4–Deoxydaunorubicin and 4–Deoxyadriamycin", J. Med. Chem. 19(12):1424 (1976).

Fischer, "The Cancer Chemotherapy Handbook" $3^{rd}$ Edition (1989), p. 88.

Salmon et al., "Antitumour Activity of Esorubicin in Human Tumour Clonogenic Assay with Comparison to Doxorubicin", J. Clin. Oncol. 2(4):282 (1984).

Kovach et al., "Phase I Trial & Assay of Rubidozone (NSC 164011) in Patients with Advanced Solid Tumors", (Mar. 1979) Cancer Research vol. 39, p. 823.

Deprez–de Campanere et al., "Pharmacokinetic, Toxicologic, and Chemotherapeutic Properties of Detorubicin in Mice: A Comparative Study with Daunourubicin and Adriamycin", Cancer Treat. Rep., 63(5):861 (1979).

Bono, "The Preclinical Development of Quelamycin and its Initial Clinical Trials.", *Aruthracyclines: Current Status and New Developments,* (1980) Academic Press, p 315.

Gosalvez et al., "Quelamycin, a New Derivative of Adriamycin with Several Possible Therapeutic Advantages", Eur. J. Cancer 14:1185 (1978).

Reich et al., "Marcellomycin *Anthracyclines: Current Status and New Developments*", (1980) Academic Press, p. 343.

Nettleston et al., New Antitumour Antibiotics: Musettamycin and Marcellomycin from Bohemic Acid Complex: (1977) 30(6) J. Antibiotics 525.

Israel et al., "Adriamycin Analogues: Preparation and Biological Evaulation of Some N–Perfluoroacyl Analogues of Daunorubicin, Adriamycin, and N–(trifluoroacetyl) adriamycin 14–valerate and their 9,10–Anhydro Derivatives" J. Med. Chem. 25:187 (1982).

Tong et al., "5–Iminodaunorubicin: Reduced Cardiotoxic Properties in an Antitumour Anthracycline", J. Med. Chem. 22(1): 36 (1979).

Arcamone et al., "Synthesis and Antitumour Activity of new Daunorubicin and Adriamycin Analogues" (1978) Experientia 34:1255.

Umezawa et al., "Tetrahydropyranyl Derivatives of Daunomycin and Adriamycin", J. Antibiot 32(10):1082 (1979).

Chen et al., "Possible Strategies for the Formulation of Antineoplastic Drugs" (1986) Drug. Dev. Ind. Pharm. vol. 12(7) 1041.

Pharmaceutics—The science of dosage form design (Aulton) (1988), pp. 242–244, 252–253, 368–369, 374–375, 380–.

Experimental Pharmaceutical Technology, $2^{nd}$ Ed.(Parrott & Saski), 1965, pp. 132–134, 149–154.

Pharmaceutics & Pharmacy Practice (1982) (Banker & Chalmers), pp. 238–243, 275–278.

Pharmaceutical Dosage Forms: Parenteral Medications: vol. 1 (Avis et al. 1984) "Biopharmaceutics of Injectable Medication" (Motola).

Connors et al., "Chemical Stability of Pharmaceuticals—a Handbook for Pharmacists" (1979) Wiley, pp. 3–7, 44–63, 74–75.

Ozturk et al., "Dissolution of Ionizable Drugs in Buffered and Unbuffered Solutions" (1988) 5(5) Pharm. Res. 272.

Gordon et al., "The Art and Science of Contemporary Drug Development", Prog. Drug. Res. 16:194 (1972).

Pharmaceutical Dosage Forms: Parenteral Medications: vol. 1 (Avis et al., 1984), "Preformulation Research of Parenteral Medications" (Motola & Agharkar).

The Theory & Practice of Industrial Pharmacy (Lachman et al.), $3^{rd}$ Ed. 1986, p. 191, et seq., pp. 191–194, 195–196, 459–460, 471–472, 477–478, 764–765.

Lin, "Kinetic Study in Formulation Investigation of New Compounds" (1968).

Zoglio, "Preformulation Stability Testing of Parenteral Products" (1968).

Knoop, "The Pharmaceutical Drug Development Process: An Overview" (1988) 22 Drug. Inf. J. 259.

Rees, "Physico–Mechanical Pre–Formulation Studies" (1973) 112 Boll. Chim. Farm. 216.

Monkhouse, "Dosage Forms For Clinical Trials" (1985) 11 (9 & 10) Drug. Dev. Ind. Pharm. 1729.

Graffner et al., "Preformulation Studies in a Drug Development Program for Tablet Formulations", J. Pharm. Sci. 74(1) 16 (1985).

Davignon et al., Pharmaceutical Aspects of Antitumour Agents (1984) Pharm. Weekbt. 119:1144.

Pharmaceutical Dosage Forms: Parenteral Medications: vol. 2 (Avis et al., 1984) "Formulation for Large Volume Parenterals" (Demorest), pp. 55–63, 68–70, 73–76, 83.

Pharmaceutical Dosage Forms: Parenteral Medications: vol. 1(Avis et al., 1984) "Formulation for Small Volume Parenterals" (DeLuca & Boylan).

Schumacher (ed), Bulk Compounding Technology.

Carlin, "Incompatibilities of Parenteral Medications" (Jun. 1968) 25 Am. J. Hosp. Pharm. 271.

Kalmas, et al., "Solubility Aspects in Parenteral Formulation" (May/Jun. 1982) Ind. J. Hosp. Pharm. 94, pp. 94–96, 98, Table I.

Parrott, Formulation of Parenterals.

Lin, "Parenteral Formulations I. Comparisons of Accelarated Stability Data with Shelf–Life Studies", Bull. Par. Drug Assoc. 23(6):269.

Lin, "Parenteral Formulations II. A Stability Testing Program for Parenteral Products", Bull. Par. Drug. Assoc. 24(2):83.

Lin, "Photochemical Considerations of Parenteral Products", Bull. Par. Drug. Assoc. 23 (4):149.

National Coordinating Committee on Large Volume Parenterals, "Recommendations to Pharmacists for Solving Problems with Large–Volume Parenterals", Am. J. Hosp. Pharm. 33:231 (1976).

Zellmer, "Solving Problems with Large–Volume Parenterals, 1: Pharmacist Responsibility for Compounding Intravenous Admixtures", Am. J. Hosp. Pharm. 32:255 (1975).

Pharmaceutical Dosage Forms, "Parenteral Medications: vol. 1 (Avis et al. 1984)—Parenteral Drug Administration: Routes, Precautions, Problems & Complications" (Duma & Akers).

Edward, "pH: An important Factor in the Compatibility of Additives In Intravenous Therapy" (Aug. 1967) vol. 24 Am. J. Hosp. Pharm. 440.

Document entitled "Kinetic pH Profiles", pp. 59–121, 380–385.

Remington's Pharmaceutical Sciences, $18^{th}$ ed. 1990; ch. 17: Ionic Solutions & Electrolytic Equilibria.

Advances in Pharmaceutical Services, vol. 2 (Bean et al., 1967), pp. 62–75, 80–95.

Fynn, "Buffers–pH Control within Pharmaceutical Systems" (Mar.–Apr. 1980) vol. 34 (2) J. Parenteral Drug Assoc. 139.

Windheuser, "The Effect of Buffers on Parenteral Solutions" (Sep./Oct. 1963) vol. 17(5) Bull Parenteral Drug Assoc.

Rubino, "The Effects of Cosolvents on the Action of Pharmaceutical Buffers" (1987) 41(2) J. Paren. Sci. Tech. 45.

Kramer & Flynn, "Solubility of Organic Hydrochlorides" (Dec. 1972) vol. 61 (12) J. Pharm. Sci. 1896.

Tencheva et al., "New Approach of the Extrapolation Procedure in the Determination of Acid–Base Constants of Poorly Soluble Pharmaceuticals" (1979); Arzneim Forsch/Drug Res. 29 (II) #9.

Bogardus et al., "Solubility of Doxycycline in Aqueous Solutions" (Feb. 1979) vol. 68 (2) J. Pharm. Sci. 188.

Miyazaki et al., "Precaution on Use of Hydrochloride Salts in Pharmaceutical Formulation" (Jun. 1981) 70(6) J. Pharm. Sci. 594.

Greene et al.: Stability of cicplatin in aqueous solution, Am J. Hosp. Pharm. 36:38 (1979).

Stjernstrom et al: Studies on the stability and compatibility of drugs in infusion fluids, Acta Pharm Spec. 15:33 (1978).
Ho: Prediction of Pharmaceutical Stability of Parenteral Solutions III (Feb. 1971) vol. 5, Drug, Int. Clin. Pharm. 47.
Stella: Chemical and Physical Bases Determining the Instability and Incompatibility of Formulated Injectable Drugs (1986) 40(4) J. Paren. Sci. Tech. 142.
Newton: "Physicochemical Determinants of Incompatibility and Instability in Injectable Drug Solutions and Admixtures" (1978 35 Am. J. Hosp. Pharm. 1213.
Mendenhall: Stability of Parenterals (1984) Drugs Dev. Ind. Pharm. 10(8–9) 1297.
Singh et al.: Effect of Solvents and Additives on the Stability of Drugs, Pharma Times 13.
Pope: Accelerated Stability Testing for Prediction of Drug Product Stability—First of a Two–Part Article (Nov., 1980) D & CI 54, pp. 54, 56, 59, 60, 62, 116.
Pope: Accelerated Stability Testing for Prediction of Drug Product Stability—Second of a Two–Part Article (Dec., 1980) D & CI 48, pp. 48, 50, 55, 56, 58, 60, 62, 64–66, 110, 112–116.
Amirjahed: Simplified Method to Study Stability of Pharmaceutical Preparations, J. Pharm. Sci. p. (6):785 (1977).
Vogenberg et al.: Stability Guidelines for Routinely Refrigerated Drug Products, Am. J. Hosp. Pharm. 40:101(1983).
Newton et al.: Estimating shelf–life of drugs in solution. Am. J. Hosp. Pharm. 44:1633 (1987).
Mollica et al.: Stability of Pharmaceuticals. J. Pharm. Sci. 67(4):443 (1978).
King et al: Statistical Prediction of Drug Stability Based on Non–Linear Parameter Extension, J. Pharm. Sci. 73(5):657.
Herrick et al.; Monetary incentive for pharmacists to control drug costs; (Jul. 1985) vol. 42, Am. J. Hosp. Pharm. 1527.
Waller: Documenting i.v. admixture product waste (Aug. 1980) vol. 43, Am. J. Hosp. Pharm. 1914.
Williams et al.: The Lyophilization of Pharmaceuticals: A Literature Review (1984) 38(2) J.. Paren. Sci. Tech. 48.

Flamberg et al.: Manufacturing Considerations in the Lyophilization of Parenteral Products (1986) Pharm. Manuf.3:29–31.
Maral et al.: Un Nouvel Antibiotique Doue D'Activite Antitumorale: La Rubidomycine (13 057 R.P.), II: Activite antitumorale experimentale Arzncimittel Forsch (1967) 17:939.
Beijnen et al.: Aspects of the Degradation Kinetics of Doxorubicin in Aqueous Solution (1986) 32 Int. J. Pharm. 123.
Gjelstrup et al., Almen Farmaci II (1983).
Handbook on Injectible Drugs $3^{rd}$ Ed. (Trissel), 1983.
Wang et al., "Review of Excipients and pH's for Parenteral Products Used in the United States", Journal of the Parenteral Drug Association 14(6):452 (1980).
Jonkman–de Vries et al., "Pharmaceutical Development of a Parental Lyophilized Formulation of the Novel Indoloquinone Antitumor Agent EO", Cancer Chemother. Pharmacol. 34:416–422 (1994).
Pharmaceutical Sciences, Mack Publishing, (1980), p. 1365–1366.
The Pharmaceutical Codex $11^{th}$ Ed., 1979, p. 446–447.
The Pharmaceutical Codex $12^{th}$ Ed. (Lund), 1994, p. 201.
Kjeld Ilver: Almen Galenisk Farmaci—Forel sningsnoter, Dansk Farmaceutforenings Forlag 1971.
Sv. Aage Schou & V. Gaun Jensen: Tr k af den glaeniske farmaci, Store Nordiske Videnskabsboghandel, 1959.
Almen Farmaci, Dansk Farmaceutforenings Forlag 1980.
Erik Sandell: Galenisk Farmaci, $2^{nd}$ edition, Stockholm 1967.
Erik Sandell: Galenisk Farmaci, $3^{rd}$ edition, Stockholm 1982.
Alfred N. Martin et al., Physikalische Pharmazie 1975, p. 239.
European Pharmacopeia, vol. III, 1979, p. 656: Citations—D 14.

INJECTABLE READY-TO-USE SOLUTIONS CONTAINING AN ANTITUMOR ANTHRACYCLINE GLYCOSIDE

This is a division of application Ser. No. 07/503,856, filed on Apr. 3, 1990, now U.S. Pat. No. 5,124,317.

The present invention relates to a stable intravenously injectable ready-to-use solution of an antitumor anthracycline glycoside, e.g. doxorubicin, to a process for preparing such a solution, and provide the same in a sealed container, and to a method for treating tumors by the use of the said ready-to-use solution.

The anthracycline glycoside compounds are a well known class of compounds in the antineoplastic group of agents, wherein doxorubicin is a typical, and the most widely used, representative: Doxorubicin. Anticancer Antibiotics, Federico Arcamone, 1981, Publ: Academic Press, New York, N.Y.; Adriamycin Review, EROTC International Symposium, Brussels, May, 1974, edited by M.Staquet, Publ. Eur. Press Medikon, Ghent, Belg.;

Results of Adriamycin Therapy, Adriamycin Symposium at Frankfurt/Main 1974 edited by M. Ghione, J. Fetzer and H. Maier, publ.: Springer, New York, N.Y.

At present, anthracycline glycoside antitumor drugs, in particular, e.g., doxorubicin, are solely available in the form of lyophilized preparations, which need to be Reconstituted before administration.

Both the manufacturing and the reconstitution of such preparations expose the involved personnel (workers, pharmacists, medical personnel, nurses) to risks of contamination which are particularly serious due to the toxicity of the antitumor substances.

The Martindale Extra Pharmacopoeia 28th edition, page 175 left column, reports, indeed, about adverse effects of antineoplastic drugs and recommends that "They must be handled with great care and contact with skin and eyes avoided; they should not be inhaled. Care must be taken to avoid extravasation since pain and tissue damage may ensue."

Similarly, Scand. J. Work Environ Health vol.10 (2), pages 71–74 (1984), as well as articles on Chemistry Industry, Issue Jul. 4, 1983, page 488, and Drug-Topics-Medical-Economics-Co, Issue Feb. 7, 1983, page 99 report about severe adverse effects observed in medical personnel exposed to use of cytostatic agents, including doxorubicin.

To administer a lyophilized preparation, double handling of the drug is required, the lyophilized cake having to be first reconstituted and then administered and,moreover,in some cases, the complete dissolution of the powder may require prolonged shaking because of solubilization problems.

As the risks connected with the manufacturing and the reconstitution of a lyophilized preparate would be highly reduced if a ready-to-use solution of the drug were available, we have developed a stable, therapeutically acceptable intravenously injectable solution of an anthracycline glycoside drug, e.g. doxorubicin, whose preparation and administration does not require either lyophilization or reconstitution.

According to the present invention, there is provided a sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate and which has a pH of from 2.5 to 6.5.

Preferably the solution of the invention is provided in a sealed container.

Preferably the anthracycline glycoside is chosen from the group consisting of doxorubicin, 4'-epi-doxorubicin (i.e. epirubicin), 4'-desoxy-doxorubicin (i.e. esorubicin), 4'-desoxy-4'-iodo-doxorubicin, daunorubicin and 4-demethoxydaunorubicin (i.e. idarubicin).

A particularly preferred anthracycline glycoside is doxorubicin.

Any physiologically acceptable salt of the anthracycline glycoside may be used for preparing the solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutammic, benzoic, methanesulfonic, ethanesulfonic and the like. The salt with hydrochloric acid is a particularly preferred salt, especially when the anthracycline glycoside is doxorubicin.

Any solvent which is physiologically acceptable and which is able to dissolve the anthracycline glycoside salt may be used. The solution of the invention may also contain one or more additional components such as a co-solubilizing agent (which may be the same as a solvent), a tonicity adjustment agent and a preservative. Examples of solvents, co-solubilizing agents, tonicity adjustment agents and preservatives which can be used for the preparation of the anthracycline glycoside solutions of the invention are hereunder reported.

Suitable solvents and co-solubilizing agents may be, for instance, water; physiological saline; aliphatic amides, e.g. N,N-dimethylacetamide, N-hydroxy-2-ethyl-lactamide and the like; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols, e.g. Brij$^R$ and the like; esters of polyoxyethylenated fatty acids, e.g. Cremophor$^R$, Myrj$^R$ and the like; polysorbates, e.g. Tweens$^R$; polyoxyethylene derivatives of polypropyleneglycols, e.g. Pluronics$^R$.

A particularly preferred co-solubilizing agent is polyvinylpyrrolidone.

Suitable tonicity adjustment agents may be, for instance, physiologically acceptable inorganic chlorides, e.g. sodium chloride, dextrose, lactose, mannitol and the like.

Preservatives suitable for physiological administration may be, for instance, esters of para-hydroxybenzoic acid (e.g., methyl, ethyl, propyl and butyl esters, or mixtures of them), chlorocresol and the like.

The above mentioned solvents and co-solubilizing agents, tonicity adjustment agents and preservatives can be used alone or as a mixture of two or more of them.

Examples of preferred solvents are water, ethanol, polyethyleneglycol and dimethylacetamide as well as mixtures in various proportions of these solvents. Water is a particularly preferred solvent.

To adjust the pH within the range of from 2.5 to about 5.0 a physiologically acceptable acid may be added as desired. The acid may be any physiologically acceptable acid, e.g., an inorganic mineral acid such as hydrochloric, hydrobromic, sulfuric, phosphoric, nitric and the like, or an organic acid such as acetic, succinic, tartaric, ascorbic, citric, glutammic, benzoic, methanesulphonic, ethanesulfonic and the like, or also an acidic physiologically acceptable buffer solution, e.g., a chloride buffer, an acetate buffer, a phosphate buffer and the like.

For obtaining pH values from about 5 to about 5.5 the addition of the acid is not, usually, necessary, but only addition of a physiologically acceptable buffer solution, e.g., one of those indicated above, may be required, as desired.

For obtaining pH values from about 5.5 to 6.5 the addition of a physiologically acceptable alkalinizing agent, such as sodium hydroxide, a mono, di- or triethanolamine or the like, or, preferably, buffer solution such as a phosphate buffer, a TRIS buffer or the like is required.

The preferred range of pH for the ready-to-use solution of the invention is from 2.5 to 5.5, in particular from about 3 to about 5.2, a pH of about 3 and a pH of about 5 being particularly preferred values.

In the solutions of the invention the concentration of the anthracycline glycoside may vary within broad ranges, preferably, from 0.1 mg/ml to 100 mg/ml, in particular from 0.1 mg/ml to 50 mg/ml, most preferably from 1 mg/ml to 20 mg/ml.

The preferred ranges of concentration may be slightly different for different anthracycline glycosides. Thus, for example, preferred concentrations for doxorubicin are from about 2 mg/ml to about 50 mg/ml, preferably from 2 mg/ml to 20 mg/ml, particularly appropriate values being 2 mg/ml and 5 mg/ml. Similar concentrations are preferred also for 4'-epi-doxorubicin, 4'-desoxy-doxorubicin and 4'-desoxy-4'-iodo-doxorubicin. Preferred ranges of concentration for daunorubicin and 4-demethoxy-daunorubicin are from 0.1 mg/ml to 50 mg/ml, preferably from 1 mg/ml to 20 mg/ml, concentrations of 1 mg/ml and 5 mg/ml being particularly appropriate.

Suitable packaging for the anthracycline glycoside solutions may be all approved containers intended for parenteral use, such as plastic and glass containers, ready-to-use syringes and the like. Preferably the container is a sealed glass container, e.g. a vial or an ampoule.

According to a particularly preferred feature of the invention, there is provided a sterile, pyrogen-free, doxorubicin solution which consists essentially of a physiologically acceptable salt of doxorubicin dissolved in a physiologically acceptable solvent therefor, which has not been reconstituted from a lyophilizate and which has a pH of from 2.5 to 6.5.

In the above indicated preferred feature of the invention the physiologically acceptable salt of doxorubicin may be, e.g. the salt with a mineral inorganic acid such as hydrochloric, hydrobromic, sulfuric, phosphoric, nitric and the like, or the salt with an organic acid such as acetic, succinic, tartaric, ascorbic, citric, glutammic, benzoic, methanesulfonic, ethanesulfonic and the like. The hydrochloride salt is a particularly preferred salt.

For the solution hereabove indicated as a preferred feature of the invention suitable solvents, co-solubilizing agents, tonicity adjustment agents and preservatives may be the same as those previously recited in this specification. Water is a particularly preferred solvent.

Also, the physiologically acceptable acid which may be added to adjust the pH to from 2.5 to about 5, if desired, and the alkanilizing agent which may be added to adjust the pH, if desired, to a value from about 5.5 to 6.5 may be one of those previously specified. When it is desired to adjust the pH of the above said preferred solution to a value of from 2.5 to about 5, hydrochloric acid is an especially preferred acid. Preferred pH values for the above said preferred solutions of the invention are from 2.5 to 5.5, in particular from about 3 to about 5.2, the pH values of 3 and 5 being especially preferred.

Though the concentration of doxorubicin in the above preferred feature may vary within the broad range from 0.1 mg/ml to 100 mg/ml, preferred concentrations are from 2 mg/ml to 50 mg/ml, most preferably from 2 mg/ml to 20 mg/ml: examples of especially preferred concentrations of doxorubicin are 2 mg/ml and 5 mg/ml.

The invention also provides a process for producing a sterile, pyrogen-free anthracycline glycoside solution with a pH of from 2.5 to 6.5, which process comprises dissolving a physiologically acceptable salt of the anthracycline glycoside, which salt is not in the form of a lyophilizate, in a physiologically acceptable solvent therefor; optionally adding a physiologically acceptable acid or buffer to adjust the pH within the said range as desired; and passing the resulting solution through a sterilising filter.

One or more additional components such as co-solubilizing agents, tonicity adjustment agents and preservatives, for instance of the kind previously specified, may be added to the solution prior to passing the solution through the sterilising filter.

With the solutions of the invention it is possible to obtain compositions having a very high concentration of the anthracycline glycoside active substance even at 50 mg/ml and more. This constitutes a great advantage over the presently available lyophilized preparates wherein high concentrations of anthracycline glycoside can only be obtained with difficulty because of solubilization problems encountered in reconstitution, mainly with saline. The presence of the excipient, e.g. lactose, in the lyophilized cake, and its generally high proportion in respect of the active substance, even up to 5 parts of excipient per part of active substance, has a negative effect on solubilization so that difficulties may arise in obtaining dissolution of the lyophilized cake, especially for concentrations of anthracycline glycoside higher than 2 mg/ml.

The solutions of the invention are characterized by a good stability. Solutions in various solvents and with different pH's and concentrations have been found to be stable for long periods at temperatures accepted for the storage of pharmaceutical preparations. This is illustrated in the Examples which follow.

Owing to the well known anti-tumor activity of the anthracycline glycoside active drug substance, the pharmaceutical compositions of the invention are useful for treating tumors in both human and animal hosts. Examples of tumors that can be treated are, for instance, sarcomas, including osteogenic and soft tissue sarcomas, carcinomas, e.g., breast-, lung-, bladder-, thyroid-, prostate- and ovarian carcinoma, lymphomas, including Hodgkin and non-Hodgkin lymphomas, neuroblastoma, melanoma, myeloma, Wilms tumor, and leukemias, including acute lymphoblastic leukemia and acute myeloblastic leukemia. Examples of specific tumours that can be treated are Moloney sarcoma Virus, Sarcoma 180 Ascites, solid Sarcoma 180, gross transplantable leukemia, L 1210 leukemia and lymphocytic P 388 leukemia. Thus, according to the invention there is also provided a method of inhibiting the growth of a tumour, in particular one of those indicated above, which comprises administering to a host suffering from said tumour an injectable solution according to the invention containing the active drug substance in an amount sufficient to inhibit the growth of said tumour. The injectable solutions of the invention are administered b rapid intravenous injection or infusion according to a variety of possible dose schedules. Suitable dose schedule for doxorubicin may be, for example, of 60 to 75 mg of active drug substance per $m^2$ of body surface given as a single rapid infusion and repeated at 21 days; an alternative schedule may be of 30 mg/$m^2$ day by intravenous route for 3 days, every 25 days. Suitable dosages for 4'-epi-doxorubicin and 4'-desoxy-doxorubicin may be, for instance, of 75 to 90 mg/$m^2$ given in a single infusion to be repeated at 21 days, and similar dosages may be useful also for 4'-desoxy-4'-iodo-doxorubicin. Idarubicin, i.e. 4-demethoxy-daunorubicin, may be. e.g., administered intravenously at a single dose of 13–15 mg//$m^2$ ever, 21 days in the treatment of solid tumours, while in the treatment of leukemias a preferred dose schedule is, e.g., of 10–12 mg/$m^2$ day by intravenous route for 3 days, to be repeated every 15–21 days; similar dosages may be, e.g., followed also for daunorubicin.

The following examples illustrate but do not limit in any way the invention.

With reference to the examples,the stability controls on the ready-to-use solutions were carried out by means of high performance liquid chromatography (HPLC), at the following

| | |
|---|---|
| Liquid chromatograph | Varian model 5010 |
| Spectrophotometric detector | Knauer model 8700 |
| Integrating recorder | Varian model CDS 401 |
| Injection valve | Rheodyne model 7125 fitted with a 10 mcl sample loop |
| Chromatographic column | Waters µ-Bondapak C18 (length = 300 mm; inner diameter = 3.9 mm; average particle size = 10 mcm) |
| Column temperature | ambient (about 22° C. ± 2° C.) |
| Mobile phase | water : acetonitrile (69:31 v/v) adjusted to pH 2 with phosphoric acid, filtered (sintered glass filter, 1 mcm or finer porosity) and deaerated |
| Mobile phase flow rate | 1.5 ml/min |
| Analytical wavelength | 254 ± 1 nm |
| Integrating recorder sensitivity | 512 |
| Chart speed | 1 cm/min |

At these conditions, the peak of the anthracycline glycoside showed a retention time of about 6 minutes. The obtained results are reported in the Tables accompanying the examples.

The extrapolation of the analytical data in order to determine the time when the 90% of the initial assay could be expected ($t_{90}$ value) was made following an Arrhenius plot.

This procedure of analytical data treatment is well known and widely used and described in the art: see, e.g., Chemical Stability of Pharmaceuticals, Kennet A. Connors, Gordon L. Amidon, Lloyd Kennon, Publ. John Wiley and Sons, New York, N.Y., 1979.

The term "teflon" refers to "Teflon™".

EXAMPLE 1

| Composition | for 80 vials | (for 1 vial) |
|---|---|---|
| Doxorubicin.HCl | 0.8 g | (10 mg) |
| Water for injections q.s. to | 0.4 l | (5 ml) |

Doxorubicin.HCl (0.80 g) was dissolved in 90 percent of the amount of water for injections, de-aerated by nitrogen bubbling. The pH of the solution was not adjusted. Further de-aerated water for injections was then added to bring the solution to its final volume (0.40 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (550° C.), 4 weeks (45° C. and 35° C.) and 12 weeks (4° C.).

The stability data obtained, using high performance liquid chromatography (HPLC) for the determination of potency, are reported in the following Table 1:

TABLE 1

INITIAL VALUES
Concentration:1.994 mg/ml   pH = 5.2
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.992 | 99.9 | 1.917 | 96.1 | 1.768 | 88.7 | 1.493 | 75.0 |
| 2 | | | 1.843 | 92.4 | 1.618 | 81.1 | 1.166 | 58.5 |
| 3 | | | 1.774 | 89.0 | 1.506 | 75.5 | 0.830 | 41.6 |
| 4 | 1.974 | 99.0 | 1.720 | 86.3 | 1.393 | 69.9 | | |
| 12 | 1.980 | 99.3 | | | | | | |

$t_{90}$ (days) extrapolated according to Arrhenius equation:
$t_{90}$ at 4° C. = 815 days
$t_{90}$ at 8° C. = 480 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 2

| Composition | for 80 vials | (for 1 vial) |
|---|---|---|
| Doxorubicin.HCl | 0.8 g | (10 mg) |
| Hydrochloric acid 0.1N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to. 3. Further de-aerated water for injections was then added to bring the solution to its final volume (0.4 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 2:

TABLE 2

INITIAL VALUES
Concentration: 1.992 mg/ml    pH = 3.0
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.995 | 100.2 | 1.952 | 98.0 | 1.919 | 96.3 | 1.493 | 75.0 |
| 2 | | | 1.889 | 94.8 | 1.851 | 92.9 | 1.036 | 51.9 |
| 3 | | | 1.876 | 94.2 | 1.565 | 78.6 | 0.730 | 36.7 |
| 4 | 1.979 | 99.4 | 1.808 | 90.8 | 1.393 | 69.9 | | |
| 12 | 1.972 | 99.0 | | | | | | |

$t_{90}$ (days) extrapolated according to Arrhenius equation:
$t_{90}$ at 4° C. = 3970 days
$t_{90}$ at 8° C. = 2000 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 3

| Composition | for 80 vials | (for 1 vial) |
|---|---|---|
| Doxorubicin.HCl | 8.0 g | (100 mg) |
| Hydrochloric acid 0.1N q.s. to | pH = 3 | (pH = 3) |
| Water for injections q.s. to | 0.4 l | (5 ml) |

Doxorubicin.HCl (8.0 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 3:

TABLE 3

INITIAL VALUES
Concentration: 20.06 mg/ml    pH = 2.95
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 20.06 | 100.0 | 19.56 | 97.5 | 17.84 | 88.9 | 12.31 | 61.4 |
| 2 | | | 18.87 | 94.1 | 15.61 | 77.8 | 7.09 | 35.3 |
| 3 | | | 18.24 | 90.9 | 13.41 | 66.8 | 3.13 | 15.6 |
| 4 | 19.91 | 99.2 | 17.51 | 87.3 | 11.07 | 55.2 | | |
| 12 | 19.80 | 98.7 | | | | | | |

$t_{90}$ (days) extrapolated according to Arrhenius equation:
$t_{90}$ at 4° C. = 3700 days
$t_{90}$ at 8° C. = 1780 days Similar stability data can be observed for analogous solutions containing 4'-epi-doxorubicin or 4'-desoxy-doxorubicin, as hydrochloride salts, at the same 20 mg/ml concentration.

EXAMPLE 4

| Composition | for 80 vials | (for 1 vial) |
|---|---|---|
| Doxorubicin.HCl | 0.80 g | (10.0 mg) |
| Polyvinylpyrrolidone | 20.00 g | (250.0 mg) |
| Water for injections q.s. to | 0.40 l | (5.0 ml) |

Doxorubicin.HCl (0.80 g) was dissolved in 90 percent of the amount of water for injections, de-aerated by nitrogen bubbling. The pH of the solution was not adjusted. Polyvinylpyrrolidone was added and dissolved under stirring and nitrogen bubbling. Further de-aerated water for injections was then added to bring the solution to its final volume (0.40 l).

The solution was filtered through a $0.22\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 4:

TABLE 4

INITIAL VALUES
Concentration: 1.986 mg/ml   pH = 4.6
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.984 | 99.9 | 1.928 | 97.1 | 1.797 | 90.5 | 1.605 | 80.8 |
| 2 | | | 1.847 | 93.0 | 1.616 | 81.4 | 1.293 | 65.1 |
| 3 | | | 1.828 | 92.0 | 1.527 | 76.9 | 1.018 | 51.3 |
| 4 | 1.928 | 97.1 | 1.797 | 90.5 | 1.403 | 70.7 | | |
| 8 | 1.989 | 100.1 | | | | | | |

$t_{90}$ (days) extrapolated according to Arrhenius equation:
$t_{90}$ at 4° C. = 1460 days
$t_{90}$ at 8° C. = 835 days Similarr stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 5

| Composition | for 80 vials | (for 1 vial) |
|---|---|---|
| Doxorubicin.HCl | 0.800 g | (10.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (0.800 g) was dissolved in 90 percent of the amount of water for injections, de-aerated by nitrogen bubbling. N,N-dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a $0.22\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 5:

TABLE 5

INITIAL VALUES
Concentration: 2.000 mg/ml      pH = 3.03
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | | | 1.892 | 94.6 | 1.735 | 86.7 | 1.495 | 74.7 |
| 2 | 1.993 | 99.7 | 1.927 | 96.4 | 1.624 | 81.2 | 1.212 | 60.6 |
| 3 | | | 1.908 | 95.4 | 1.432 | 71.6 | 1.032 | 51.6 |
| 4 | 2.00 | 100.0 | 1.863 | 93.2 | 1.266 | 63.3 | | |
| 8 | 1.960 | 98.0 | | | | | | |

$t_{90}$ (days) extrapolated according to Arrhenius equation:
$t_{90}$ at 4° C. = 4360 days
$t_{90}$ at 8° C. = 2200 days Similar stability data can be observed also for analogous solutions containing either doxorubicin hydrochloride at 5 mg/ml concentration, or 4'-epi-doxorubicin, 4'-desoxy-doxorubicin, 4'-desoxy-iodo-doxorubicin, daunorubicin or 4-demethoxy-daunorubicin, hydrochloride salts, at both 2 mg/ml and 5 mg/ml concentration.

EXAMPLE 6

| Composition | for 80 vials | (for 1 vial) |
|---|---|---|
| Doxorubicin.HCl | 0.8 g | (10.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (0.8 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22$\mu$ microporous membrane under nitrogen pressure. Volumes of 5 ml of the solution were distributed into type I-colourless glass vials The solution was filtered through a 0.22$\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 6;

TABLE 6

INITIAL VALUES
Concentration: 1.973mg/ml      pH = 2.71
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 2.028 | 102.8 | 1.944 | 98.5 | 1.791 | 90.8 | 1.477 | 74.9 |
| 2 | | | 1.885 | 95.5 | 1.582 | 80.2 | 0.972 | 49.3 |
| 3 | | | 1.840 | 93.2 | 1.402 | 71.0 | 0.632 | 32.0 |
| 4 | 1.913 | 97.0 | 1.853 | 93.9 | 1.273 | 64.5 | | |
| 8 | 1.972 | 99.9 | | | | | | |

$t_{90}$ (days) extrapolated according to Arrhenius equation:
$t_{90}$ at 4° C. = 5560 days
$t_{90}$ at 8° C. = 2670 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 7

| Composition | for 80 vials | (for 1 vial) |
|---|---|---|
| Doxorubicin.HCl | 8.00 g | (100.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (8.00 g) was dissolved in 90 percent of the amount of water for injections, de-aerated by nitrogen bubbling. N,N-dimethylacetamide was added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 7:

Similar stability data can be observed for analogous solutions containing 4'-epi-doxorubicin or 4'-desoxy-doxorubicin, as hydrochloride salts, at the same 20 mg/ml concentration.

EXAMPLE 8

| Composition | for 80 vials | (for 1 vial) |
|---|---|---|
| Doxorubicin.HCl | 0.80 g | (10.0 mg) |
| Ethanol | 0.12 l | (1.5 ml) |
| Hydrochloric acid 0.1 N q.s. to | pH = 3 | (pH = 3) |
| Water for injections q.s. to | 0.40 l | (5.0 ml) |

Doxorubicin.HCl (0.80g) was dissolved in 90 percent of the amount of water for injections, de-aerated by nitrogen bubbling. Ethanol was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and at 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 8.

TABLE 7

INITIAL VALUES
Concentration: 19.32 mg/ml    pH = 2.96
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 20.1 | 103.5 | 19.14 | 99.1 | 17.34 | 89.8 | 15.57 | 80.6 |
| 2 | | | 19.20 | 99.4 | 15.77 | 81.6 | 12.94 | 67.0 |
| 3 | | | 18.06 | 93.5 | 14.85 | 76.9 | 11.61 | 60.1 |
| 4 | 20.03 | 103.7 | 17.81 | 92.2 | 13.78 | 71.3 | | |
| 8 | 19.99 | 103.5 | | | | | | |

$t_{90}$ (days) extrapolated according to Arrhenius equation:
$t_{90}$ at 4° C. = 1310 days
$t_{90}$ at 8° C. = 770 days

TABLE 8

INITIAL VALUES
Concentration: 1.979 mg/ml    pH = 3.11
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 2.010 | 101.6 | 1.965 | 99.3 | 1.947 | 98.4 | 1.750 | 88.4 |
| 2 | | | 1.957 | 98.9 | 1.910 | 96.5 | 1.645 | 83.1 |
| 3 | | | 1.895 | 95.8 | 1.737 | 87.8 | 1.356 | 68.5 |
| 4 | 1.927 | 97.3 | 1.818 | 91.9 | 1.678 | 84.8 | | |
| 12 | 1.939 | 97.9 | | | | | | |

$t_{90}$ (days) extrapolated according to Arrhenius equation:
$t_{90}$ at 4° C. = 1270 days
$t_{90}$ at 8° C. = 780 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 9

| Composition | for 80 vials | (for 1 vial) |
|---|---|---|
| Doxorubicin.HCl | 8.000 g | (100.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (8.000 g) was dissolved in 90 percent of the amount of water for injections, de-aerated by nitrogen bubbling. N,N-dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a $0.22\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 9:

TABLE 9

INITIAL VALUES
Concentration: 20.07 mg/ml    pH = 2.99
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | | | 19.14 | 95.4 | 17.81 | 88.7 | 14.84 | 73.9 |
| 2 | 19.97 | 99.5 | 19.07 | 95.0 | 16.27 | 81.1 | 12.36 | 61.6 |
| 3 | | | 18.08 | 90.1 | 14.62 | 72.9 | 10.04 | 50.0 |
| 4 | 20.06 | 99.9 | 18.03 | 89.8 | 13.20 | 65.8 | | |
| 8 | 19.69 | 98.1 | | | | | | |

$t_{90}$ (days) extrapolated according to Arrhenius equation:
$t_{90}$ at 4° C. = 846 days
$t_{90}$ at 8° C. = 505 days Similar stability data can be observed for analogous solutions containing 4'-epi-doxorubicin or 4'-desoxy-doxorubicin, as hydrochloride salts, at the same 20 mg/ml concentration.

EXAMPLE 10

| Composition | for 80 vials | (for 1 vial) |
|---|---|---|
| Doxorubicin.HCl | 8.0 g | (100.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (8.0 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45°C. and 35° C.) and 8 weeks (4° C.).

The stability data obtained, using high performance liquid chromatography (HPLC) for the determination of potency, are reported in the following Table 10:

TABLE 10

INITIAL VALUES
Concentration: 19.57 mg/ml  pH = 2.62
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 19.54 | 99.9 | 19.11 | 97.6 | 16.88 | 86.2 | 12.48 | 63.8 |
| 2 | | | 18.43 | 94.2 | 14.13 | 72.2 | 6.00 | 30.7 |
| 3 | | | 18.02 | 92.1 | 11.57 | 59.1 | 2.61 | 13.3 |
| 4 | 19.58 | 100.1 | 17.36 | 88.7 | 9.23 | 47.2 | | |
| 8 | 19.34 | 98.8 | | | | | | |

$t_{90}$ (days) extrapolated according to Arrhenius equation:
$t_{90}$ at 4° C. = 2540 days
$t_{90}$ at 8° C. = 1290 days Similar stability data can be observed for analogous solutions containing 4'-epi-doxorubicin or 4'-desoxy-doxorubicin, as hydrochloride salts, at the same 20 mg/ml concentration.

EXAMPLE 11

| Composition | for 80 vials | (for 1 vial) |
|---|---|---|
| Doxorubicin.HCl | 0.80 g | (10.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. N,N-Dimethylacetamide was added under stirring and nitrogen bubbling. Hydrochloric acid 0.1N was then added dropwise to adjust the pH of the solution to 3. De-aerated water for injections was finally added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 11:

TABLE 11

INITIAL VALUES
Concentration: 1.826 mg/ml    pH = 3.14
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.830 | 100.2 | 1.812 | 99.2 | 1.784 | 97.7 | 1.605 | 87.9 |
| 2 | 1.818 | 99.6 | 1.781 | 97.5 | 1.554 | 85.1 | 1.292 | 70.8 |
| 3 | | | 1.743 | 95.4 | 1.409 | 77.2 | 1.018 | 55.7 |
| 4 | 1.823 | 99.8 | 1.734 | 95.0 | 1.369 | 75.0 | | |
| 8 | 1.792 | 98.2 | | | | | | |

$t_{90}$ (days) extrapolated according to Arrhenius equation:
$t_{90}$ at 4° C. = 5815 days
$t_{90}$ at 8° C. = 2920 days Similar stability data can be observed also for analogous solutions containing either doxorubicin hydrochloride at 5 mg/ml concentration, or 4'-epi-doxorubicin, 4'-desoxy-doxorubicin, 4'-epi-desoxy-4'-iodo-doxorubicin, daunorubicin or 4-demethoxy-daunorubicin, as hydrochloride salts, at both 2 mg/ml and 5 mg/ml concentration.

EXAMPLE 12

| Composition | for 80 vials | (for 1 vial) |
|---|---|---|
| Doxorubicin.HCl | 0.80 g | (10.0 mg) |
| Propylene glycol | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections de-aerated by nitrogen bubbling. Propylene glycol was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a $0.22\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 12:

TABLE 12

INITIAL VALUES
Concentration: 1.982 mg/ml    pH = 3.11
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.972 | 99.5 | 1.934 | 97.6 | 1.889 | 95.3 | 1.705 | 86.0 |
| 2 | | | 1.952 | 98.5 | 1.795 | 90.6 | 1.483 | 74.8 |
| 3 | | | 1.935 | 97.6 | 1.699 | 85.7 | 1.153 | 58.2 |
| 4 | 2.056 | 103.7 | 1.788 | 90.2 | 1.460 | 73.7 | | |

$t_{90}$ (days) extrapolated according to Arrhenius equation:
$t_{90}$ at 4° C. = 1794 days
$t_{90}$ at 8° C. = 1025 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml 5 mg/ml concentration.

EXAMPLE 13

| Composition | for 80 vials | (for 1 vial) |
|---|---|---|
| Doxorubicin.HCl | 0.80 g | (10.0 mg) |
| Polyethylene glycol 400 | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. Polyethylene glycol 400 was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 13:

TABLE 13

INITIAL VALUES
Concentration: 1.907 mg/ml    pH = 3.07
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel.% Assay | Conc. mg/ml | Rel.% Assay | Conc. mg/ml | Rel.% Assay | Conc. mg/ml | Rel.% Assay |
| 1 | 1.871 | 98.1 | 1.797 | 94.2 | 1.668 | 87.5 | 1.484 | 77.8 |
| 2 | | | 1.710 | 89.7 | 1.608 | 84.3 | 1.237 | 64.9 |
| 3 | | | 1.739 | 91.2 | 1.551 | 81.3 | 1.007 | 52.8 |
| 4 | 1.873 | 98.2 | 1.693 | 88.8 | 1.453 | 76.2 | | |

$t_{90}$ (days) extrapolated according to Arrhenius equation:
$t_{90}$ at 4° C. = 1130 days
$t_{90}$ at 8° C. = 680 days Similar stability data can be observed also for analogous solutions containing either doxorubicin hydrochloride at 5mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 14

| Composition | for 80 vials | (for 1 vial) |
|---|---|---|
| Doxorubicin.HCl | 0.8 g | (10 mg) |
| Hydrochloric acid 0.1N | pH = 3 | (pH = 3) |
| q.s. to Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 4° C. and 8° C. for up to 6 months.

The stability data obtained, using high performance liquid chromatography (HPLC) for the determination of potency, are reported in the following Table 14:

TABLE 14

INITIAL VALUES
Concentration: 2.039 mg/ml    pH = 3.06
Relative % Assay: 100.0

| | TEMPERATURE | | | |
|---|---|---|---|---|
| | 4° C. | | 8° C. | |
| TIME (months) | Conc. mg/ml | Rel.% Assay | Conc. mg/ml | Rel.% Assay |
| 1 | 1.983 | 97.3 | 1.959 | 96.1 |
| 3 | 1.984 | 97.3 | 1.983 | 97.3 |
| 6 | 2.012 | 98.7 | 2.002 | 98.2 |

At the same conditions, similar stability data can be generally observed also for the other solutions mentioned in the preceding examples.

We claim:

1. A physiologically acceptable solution of anthracycline glycoside selected from the group consisting of idarubicin hydrochloride, doxorubicin hydrochloride and epirubicin hydrochloride dissolved in a physiologically acceptable aqueous solvent, having a pH adjusted to from 2.5 to 5.0 with a physiologically acceptable acid selected from the group consisting of hydrochloric acid, sulfuric acid, phosphoric acid, methane sulfonic acid, and tartaric acid, the concentration of said anthracycline glycoside being from 0.1 to 100 mg/ml, wherein said solution is contained in a sealed container.

2. The solution of claim 1 wherein said physiologically acceptable aqueous solvent is selected from the group consisting of water, ethanol, polyethylene glycol, dimethylacetamide, and mixtures thereof.

3. The solution of claim 1 wherein the physiologically acceptable aqueous solvent is water.

4. The solution of claim 1 wherein the concentration of the doxorubicin is from 0.1 to 50 mg/ml.

5. The solution of claim 4 wherein the concentration of doxorubicin is from 1 to 20 mg/ml.

6. The solution of claim 1 wherein the concentration of doxorubicin is about 2 mg/ml.

7. The solution of claim 1 wherein the concentration of doxorubicin is about 5 mg/ml.

8. A sealed container containing a stable, intravenously injectable, sterile, pyrogen-free doxorubicin solution which consists essentially of doxorubicin hydrochloride dissolved in a physiologically acceptable solvent therefore, wherein said solution has a pH adjusted to 2.71 to 3.14 with a physiologically acceptable acid and has a concentration of doxorubicin of from 0.1 to 100 mg/ml.

9. The anthracycline glycoside solution of claim 1, wherein said solution exhibits storage stability as a result of said pH being adjusted to the said pH range using said acids.

10. The container of claim 8, wherein said doxorubicin solution exhibits storage stability as a result of said pH being adjusted to the said pH range using said acids.

11. The solution of claim 1 wherein the concentration of anthracycline glycoside is about 1 mg/ml.

12. The solution of claim 11 wherein the physiologically acceptable acid is hydrochloric acid.

13. The solution of claim 12 wherein the anthracycline glycoside is idarubicin hydrochloride.

* * * * *

UNITED STATES PATENT AND TRADEMARK OFFICE
CERTIFICATE OF CORRECTION

PATENT NO. : 6,107,285
DATED : August 22, 2000
INVENTOR(S) : Gaetano Gatti et al It is certified that error appears in the above-identified patent and that said Letters Patent is hereby corrected as shown below:

Title page,
Item [56], Reference Cited, U.S. PATENT DOCUMENTS; please insert
-- 3,803,124 4/1974 Arcamone et al. --;
FOREIGN PATENT DOCUMENTS please insert -- 3621844 A1 3/1987 Germany --;
please insert -- 1,291,037 1991/10/22 Canada --;
OTHER PUBLICATIONS; please insert the following references:
-- Beijnen et al. (1985), Stability of Anthracycline Antitumor Agents in Infusion Fluids," J. Parenteral Science and Technology, Vol. 39, pp. 220-222.

Daugherty et al. (1981), "Photolytic Destruction of Adriamycin," J. Pharm. Pharmacol. Vol.33, p. 556.

Dorr and Fritz (1980), "Doxorubicin," Cancer Chemotherapy Handbook, Elsevier, New York, pp. 388-401.

Flora et al. (1980), "The Loss of Paraben Preservatives During Freeze Drying," J. Pharm. Pharmacol., vol. 32, pp. 577-578.

Florence and Atwood (1981), "Physicochemical Principles of Pharmacy," MacMillan Press, London, p. 475.

Garnick et al. (1983), "Clinical Evaluation of Long-Term, Continuous Infusion Doxorubicin," Cancer Treatment Reports, vol. 67, pp. 133-142.

Henry, D. W. (1976), "Adriamycin," Cancer Chemotherapy, American Chemical Society Symposium Series, pp. 15-57.

Kaniewska, T. (1977), "A Study of Decomposition of Adriamycin," Pharmacia Polska, vol. 9, 539-542.

Ketchum et al. (1981), "Cost Benefit and Stability Study of Doxorubicin Following Reconstitution," Am. J. Intravenous Therapy & Clinical Nutrition, vol. 8, pp. 15-18.

Kristensen and Moller (1983), "Almen Farmaci II," Dansk Farmaceutforeigs Forlag, Kobenhavn, pp. 408, 442, 447.

Menozzi et al. (1984), "Self Association of Doxorubicin and Related Compounds in Aqueous Solution," J. Pharamaceutical Sciences, vol. 73, pp. 766-770.

Savlov et al. (1981), "Comparison of Doxorubicin With Cycloleucine in the treatment of Sarcomas," Cancer Treatment Sciences, vol. 65, pp. 21-27.

Trissell (1980), "Doxorubicin HCl," Handbook of Injectable Drugs, Third Ed. (American Society of Hospital Pharmacists, Bethesda, MD), pp. 131-132.

Williamson et al. (1980), "Doxorubicin Hydrochloride-Aluminium Interaction," Am. J. Hospital Pharmacy, vol. 40, p. 214.

Drug Topics, "Cancer Drug Danger," February 7, 1983, p. 99.

Gutteridge and Wilkins (1983), "Doxorubicin Degradation: Changes in Activity Compared by Bacterial Growth Inhibition and Free Radical-Dependent Damage to Deoxyribose," J. Biological Standardization, vol. 11, pp. 359-364.

UNITED STATES PATENT AND TRADEMARK OFFICE
CERTIFICATE OF CORRECTION

PATENT NO.   : 6,107,285
DATED        : August 22, 2000
INVENTOR(S)  : Gaetano Gatti et al It is certified that error appears in the above-identified patent and that said Letters Patent is hereby corrected as shown below:

Akbiyik et al. (1979), "Total Lung Irradiation and Chemeotherapy in Pulmonary Metastates from Carcinoma of the Uterine Cervix and Endometrium," J. Nat'l Medical Assn., vol. 71, pp. 1061-1063.
      Swinyard, E. A. (1980), "Introductin of New Drugs," Pharmaceutical Sciences, Mack Publishing Co., Easton, Pennsylvania, pp. 1365-1076.
      Nikula et al. (1984). "Chromosome Aberrations in Lymphocytes of Nurses Handling Cystostatic Agents," Scand. J. Work Environ. Health, vol. 10, pp. 71-74.
      U.S. Pharmacopoeia, "Doxorubicin Hydrochloride for Injection," 20th revision, p. 266.
U.S. Pharmacopoeia (1985), p. 119.
Formularium Der Nederlandse Apothekers, Band V (1983), p. I.8, I.24, I.63-1.64a, I.82, I.88.
      Yoo (1977), Section "Injections" in the Korean Pharmacopoeia, pp. 3, 48-49.
      Harris, D. C. (1995), Quantitative Chemical Analysis, Fourth Edition, W. H. Freeman & Company, New York, pp. 23ochloric Acid," S. Budavari, Ed., Merck & Co., Inc., Rahway, New Jersey, No. 4703, p. 756.
      The Merck Index (1989), "Aclacinomycins," S. Budavari, Ed., Merck & Co., Inc., Rahway, New Jersey, No. 108, p.17.
      Trissell, L. A. (1983), "Investigational Drugs," Handbook on Injectable Drugs, Third Edition, American Society of Hospital Pharmacists.
      German Patent Office Decision dated October 8, 1996 revoking Patent No. 36 21844.
      Harris, D. C. (1995), "Quantitative Chemical Analysis," 4th Edition, W. H. Freeman and Company. --

Item [56], References Cited, OTHER PUBLICATIONS; please insert the following references:
    -- Bradner and Misiek, (1977) *The Journal of Antibiotics*, "Bohemic Acid Complex. Biological Characterization of the Antibiotics, Musettamycin and Marcellomycin," 30(6)519-522.
      Kjeld Ilver, *Almen Galenisk Farmaci-Forelœsningsnoter*, Dansk Farmaceutforenings Forlag 1971, pp. 132-136. (English translation provided)
      Gjelstrup et al. (1983), *Almen Farmaaci I*, Dansk Farmaceutforenings Forlag, København, pp. 404-408, 440, 442-443, 447, 451. (English translation provided)
Erik Sandell, (1967), *Galenisk Farmaci*, $2_{nd}$ edition, Stockholm, pp. 214. (English translation provided)

UNITED STATES PATENT AND TRADEMARK OFFICE
CERTIFICATE OF CORRECTION

PATENT NO.    : 6,107,285
DATED         : August 22, 2000
INVENTOR(S)   : Gaetano Gatti et al It is certified that error appears in the above-identified patent and that said Letters Patent is hereby corrected as shown below:

Erk Sandell, (1982), *Galenisk Farmaci*, 3$^{rd}$ edition Stockholm, pp. 123. (English translation provided)
    Svend Aage Schou & V. Gaunø Jensen (1959), *Troek af den flaeniske farmaci*, Store Nordiske Videnskabsboghandel, pp. 220. (English translation provided)
    Arcamone, F. (1977), *Lloydia*, "New Antitumor Anthracyclines," 40(1):45-66.
    Naff et al., (1982) *Anthracycline Antibiotics*, "Anthracyclines in the National Cancer Institute Program, Hassan S. El Khadam, editor, Academic Press, pp. 1-57.
    *Formularium Der Nederlandse Apothekers*, (1983) pp..I.8, I.24, I.63.
    *Formularium DerNederlandse Apothekers*, (1979) pp. I.64, I.82.
    *Formularium Der Nederlandse Apothekers*, (1985) pp. I.64a.
    *Formularium Der Nederlandse Apothekers*, (1989) pp. I.88.
    *Formularium Der Nederlandse Apothekers*, (1992) pp. I.63a.

Harris, *Quantitative Chemical Analysis*, Fourth Edition, W.H. Freeman & Company, New York, pp. 240.
    Bernard et al., editors (1969), *Rubidomycin A New Agent Against Cancer*, pp. ix-181.--;

Column 4,
Line 57, please delete "mg//m$^2$" and insert -- mg/m$^2$ --;
Line 67, after "following" please insert -- experimental conditions: --;

Column 6,
Line 15, please delete "550° C" and insert -- 55° C --;

UNITED STATES PATENT AND TRADEMARK OFFICE
CERTIFICATE OF CORRECTION

PATENT NO. : 6,107,285
DATED : August 22, 2000
INVENTOR(S) : Gaetano Gatti et al It is certified that error appears in the above-identified patent and that said Letters Patent is hereby corrected as shown below:

Column 9,
Line 59, please delete "Similarr" and insert -- Similar --;

Column 12,
Lines 21-23, please delete "The solution was filtered through a 0.22μ microporous membrane under nitrogen pressure. Volumes of 5 ml of the solution were distributed into type I colourless glass vials"; and Column 24,
Line 9, Please delete "2.71 to 3.14" and insert -- 2.5 to 5.0 --.

Signed and Sealed this

Twenty-first Day of May, 2002

*Attest:*

JAMES E. ROGAN
*Attesting Officer*     Director of the United States Patent and Trademark Office

UNITED STATES PATENT AND TRADEMARK OFFICE
CERTIFICATE OF CORRECTION

PATENT NO.   : 6,107,285
DATED        : August 22, 2000
INVENTOR(S)  : Gaetano Gatti et al.

Page 1 of 1

It is certified that error appears in the above-identified patent and that said Letters Patent is hereby corrected as shown below:

<u>Title page,</u>
Item [62], Related U.S. Application Data, after "Pat. No. 5,124,317" please insert -- , which is a division of application No. 07/385,999, filed on Jul. 27, 1989, now Pat. No. 4,946,831, which is a continuation of application No. 06/878,784, filed on Jun. 26, 1986, now abandoned --.

<u>Column 1,</u>
Line 6, after "U.S. Pat. No. 5,124,317" please insert -- , which is a division of application No. 07/385,999, filed on Jul. 27, 1989, now Pat. No. 4,946,831, which is a continuation of application No. 06/878,784, filed on Jun. 26, 1986, now abandoned --.

Signed and Sealed this

Eighteenth Day of May, 2004

JON W. DUDAS
*Acting Director of the United States Patent and Trademark Office*